(12) United States Patent
Sun et al.

(10) Patent No.: US 12,678,480 B2
(45) Date of Patent: Jul. 14, 2026

(54) POLYPEPTIDE APPLIED TO INHIBITION OF INTRACELLULAR LIPID ACCUMULATION AND SYNTHESIS METHOD THEREOF

(71) Applicant: NATIONAL CHENG KUNG UNIVERSITY, Tainan City (TW)

(72) Inventors: Hungyu Sun, Tainan (CN); Nong Qin, Changsha (CN); Yungchun Chuang, Tainan (CN); Yuwei Cheng, Tainan (CN); Shuangdi Duan, Changsha (CN); Yating Gao, ChangSha (CN); Kung-Chia Young, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 533 days.

(21) Appl. No.: 18/576,106

(22) PCT Filed: Mar. 4, 2022

(86) PCT No.: PCT/CN2022/079288
§ 371 (c)(1),
(2) Date: Jan. 3, 2024

(87) PCT Pub. No.: WO2022/184165
PCT Pub. Date: Sep. 9, 2022

(65) Prior Publication Data
US 2024/0366713 A1 Nov. 7, 2024

(30) Foreign Application Priority Data
Mar. 5, 2021 (CN) .......................... 202110245720.4

(51) Int. Cl.
*A61K 38/16* (2006.01)
*C07K 1/04* (2006.01)

(52) U.S. Cl.
CPC .............. *A61K 38/16* (2013.01); *C07K 1/042* (2013.01)

(58) Field of Classification Search
CPC ................................ A61K 38/16; C07K 1/042
See application file for complete search history.

(56) References Cited

FOREIGN PATENT DOCUMENTS

| | | |
|---|---|---|
| CN | 110520143 A | 11/2019 |
| CN | 113121650 A | 7/2021 |
| CN | 113121650 B | 1/2022 |
| KR | 20150117185 A | 10/2015 |
| WO | 2004113501 A2 | 12/2004 |

OTHER PUBLICATIONS

Mengshi Pan, et al., Positively charged peptides from casein hydrolysate show strong inhibitory effects on LDL oxidation and cellular lipid accumulation in Raw264.7 cells, International Dairy Journal, 2019, pp. 119-128, vol. 91.
Liu Jian, et al., Effects of Liraglutide on Renal Lipid Deposition of Obese Rats, Journal of Chengde Medical College, 2016, pp. 1-6, vol. 33, No. 1.

*Primary Examiner* — Amber D Steele
(74) *Attorney, Agent, or Firm* — CKC & Partners Co., LLC

(57) ABSTRACT

A biological polypeptide applied to inhibition of intracellular lipid accumulation and a synthesis method thereof are provided. An amino acid sequence of the polypeptide is shown in SEQ ID NO: 1 in sequence listing. The polypeptide has relatively high target affinity and high activity, and can exhibit remarkably high activity at extremely low dosages and concentrations. The polypeptide inhibits binding of clusterin and sterol O-acyltransferase by exerting competition on the clusterin to reduce the activity of the sterol O-acyltransferase, so as to achieve functions of controlling physiological metabolism in organisms, such as relieving lipid accumulation in hepatocytes, resisting tumor occurrence, assisting anti-cancer drugs in inhibiting tumor growth, and the like. A synthesis process of the polypeptide is simple; the molecular weight of the polypeptide is small, and the artificial synthesis efficiency is high; through a solid-phase synthesis method, the difficulty of product purification in each step is greatly reduced.

11 Claims, 8 Drawing Sheets

Specification includes a Sequence Listing.

POLYPEPTIDE APPLIED TO INHIBITION OF INTRACELLULAR LIPID ACCUMULATION AND SYNTHESIS METHOD THEREOF

CROSS REFERENCE TO THE RELATED APPLICATIONS

This application is the national phase entry of International Application No. PCT/CN2022/079288, filed on Mar. 4, 2022, which is based upon and claims priority to Chinese Patent Application No. 202110245720.4, filed on Mar. 5, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBGZZL002_Sequence_Listing.txt, created on Dec. 11, 2023, and is 929 bytes in size.

TECHNICAL FIELD

The present disclosure belongs to the technical field of biological polypeptides, and particularly relates to a polypeptide applied to inhibition of intracellular lipid accumulation and a synthesis method thereof.

BACKGROUND

With the development of economy, NAFLD (non-alcoholic fatty liver disease) has become the most common liver disease in the world. According to epidemiological statistics, patients with NAFLD account for about 25% of the global population. Especially in economically developed countries, e.g., the United States, about 30-40% of adults suffer from NAFLD. In 2016, NAFLD caused an annual economic loss of about 103 billion dollars to the United States. NAFLD is a chronic liver disease caused by metabolic syndrome, mainly characterized by great fat accumulation in liver cells; although the pathological process can be alleviated or even reversed through diet control and regular exercise in the early stage, most patients fail to achieve or maintain dietary goals and weight loss; and with the continuous increase of lipid accumulation, the liver damage worsens. Non-alcoholic liver disease can develop into hepatitis, cirrhosis and even liver cancer, which greatly threatens human life and health. Since the early symptoms of NAFLD are not obvious, NAFLD is difficult to be detected early, so it is particularly necessary to relieve liver lipid accumulation in time.

SUMMARY

In view of the above-mentioned problems, an objective of the present disclosure is to provide a polypeptide applied to inhibition of intracellular lipid accumulation and a synthesis method thereof. The polypeptide has high target affinity and high activity, and has the functions of relieving lipid accumulation in hepatocytes, resisting tumor occurrence, assisting anti-cancer drugs in inhibiting tumor growth.

The technical content of the present disclosure is as follows:

the present disclosure provides a polypeptide applied to inhibition of intracellular lipid accumulation. An amino acid sequence of the polypeptide is shown in SEQ ID NO: 1 in sequence listing, where peptide segments 1-41 of the amino acid sequence are functional peptide segments playing a role of inhibiting fat accumulation; peptide segments 42-53 of the amino acid sequence are cell-penetrating peptides assisting the polypeptide in entering cells. Any means that can assist the functional peptide segments 1-41 in entering cells, such as the transgenic process and carrying different cell-penetrating peptides, and the like, can achieve the effect of inhibiting intracellular lipid accumulation.

The present disclosure also provides a polypeptide applied to inhibition of intracellular lipid accumulation, for use in preparing polypeptide drugs.

The present disclosure also provides a synthesis method of a polypeptide applied to inhibition of intracellular lipid accumulation, which includes the following steps:

1) soaking a resin in an organic solution, washing off the organic solution, removing a protecting group on the resin with a deprotecting agent (uncapping), and washing the obtained resin;

2) taking a second amino acid at free carboxyl terminal, adding a condensing agent and DMF into the above resin for reaction, and then taking the resin for color testing;

3) removing a protecting group on the second amino acid with the deprotecting agent (uncapping), and washing the obtained product;

4) repeating step 2) and step 3) for connection of amino acids until the last amino acid is connected;

5) removing a protecting group on the last amino acid with the deprotecting agent (uncapping), washing and then subjecting the obtained resin to color testing; and 6) after completion of the reaction, washing and shrinking a polypeptide product with a solution, digesting the polypeptide product by a lysis buffer to obtain a polypeptide, and finally, analyzing and purifying the obtained polypeptide;

the resin in step 1) includes Fmoc-lys (boc) Wang resin;

the organic solution in step 1) includes dichloromethane (DCM);

the deprotecting agent in step 1), step 3) and step 5) includes amine-base solvents, specifically one of piperidine, concentrated ammonia, dioxane/4M NaOH, ethanolamine, cyclohexylamine, morpholine, pyrrolidone and 1,8-Diazabicyclo[5,4,0]undec-7-ene (DBU), and preferably 20% piperidine;

a reagent for the washing in step 1), step 3) and step 5) is DMF (N,N-dimethylformamide);

the color testing in step 2) is a ninhydrin color testing reaction, and a color result is that the solution is bright yellow, the resin is transparent, and there is no mixed color;

the color testing in step 5) is a ninhydrin color testing reaction, a blue color result of the color testing indicates that the protecting groups are successfully removed, and a colorless result indicates that no reaction occurs and an additional uncapping operation is needed.

in step 6), the solution includes DCM and MeOH; and the lysis buffer is a mixed solution of trifluoroacetic acid, 1,2-ethanedithiol and water.

Peptide synthesis is a process of repeatedly adding amino acids, and a solid-phase synthesis sequence is generally a sequence of synthesis from C-terminal (carboxyl terminal) to N-terminal (amino terminal). The use of a solid-phase synthesis method greatly reduces the difficulty of product purification in each step. In order to prevent the occurrence of side reactions, side chains of the amino acids participating in the reaction are protected, while the carboxyl terminals are free and must be activated before the reaction. The C-terminal refers to the carboxy terminal, and in case of counting from the carboxy terminal, the free carboxy terminal is the first amino acid.

Compared with the prior art, the present disclosure has the beneficial effects as follows:

the polypeptide applied to inhibition of intracellular lipid accumulation provided by the present disclosure has relatively high target affinity and high activity, and can exhibit remarkably high activity at extremely low dosages and concentrations, and a hydrolysis product of the polypeptide is an amino acid which is non-toxic;

the polypeptide provided by the present disclosure inhibits binding of clusterin and sterol O-acyltransferase by exerting competition on the clusterin to reduce the activity of the sterol O-acyltransferase, so as to achieve functions of controlling physiological metabolism in organisms, such as relieving lipid accumulation in hepatocytes, resisting tumor occurrence, assisting anticancer drugs in inhibiting tumor growth and the like;

the polypeptide provided by the present disclosure, by inhibiting liver lipid accumulation, alleviates and treats NAFLD and prevents the occurrence of cirrhosis or liver cancer so as to protect the life and health of patients, and relieves social and economic burdens caused by NAFLD, and metabolites of the peptide of the present disclosure are non-toxic and can be removed by proteolytic degradation and renal filtration; and a synthesis process of the polypeptide is simple; the molecular weight of the polypeptide is small, and the artificial synthesis efficiency is high; through a solid-phase synthesis method, the difficulty of product purification in each step is greatly reduced; and process automation, easy control and low cost are achieved. In order to prevent the occurrence of side reactions, side chains of the amino acids participating in the reaction are protected.

DETAILED DESCRIPTION OF THE EMBODIMENTS

The present disclosure will be described below in further detail with reference to specific examples and the drawings. It should be understood that these examples are only used to illustrate the present disclosure and not to limit the scope of protection of the present disclosure. Any modifications in various equivalent forms, made by those skilled in the art to the present disclosure after reading the present disclosure, all fall within the scope defined by the appended claims of the present application.

Unless otherwise specified, all raw materials and reagents of the present disclosure are conventionally available raw materials and reagents.

Example 1

A polypeptide applied to inhibition of intracellular lipid accumulation and synthesis thereof:

1) 1 g of Fmoc-lys (boc) Wang resin was put into a reaction column, 1.5 g of DCM was added to soak the resin for 5 min, 2 g of DMF was used to wash off the DCM, 2 g of 20% piperidine as a deprotecting agent was used to remove the Fmoc protecting group on the resin where the uncapping time was 20 min, then the resin was washed with the DMF for 6 times, and was subjected to color testing, where a blue color result indicated that the Fmoc was successfully removed, and a colorless result indicated that no reaction occurred and additional uncapping was needed;

2) a second amino acid (arg) at free carboxyl terminal was taken, 2 g of a condensing agent DIC and 2 g of DMF were added into the resin reaction column for reaction (gas bubbling), and then the resin was taken for a ninhydrin color testing reaction, where a color result was that the solution was bright yellow, the resin was transparent, and there was no mixed color;

3) 2 g of 20% piperidine as a deprotecting agent was used to remove the Fmoc protecting group on the second amino acid, and the resin was washed with the DMF for 6 times, and was subjected to color testing, where a blue color result indicated that the Fmoc was successfully removed, and a colorless result indicated that no reaction occurred and additional uncapping was needed;

4) step 2) and step 3) were repeated for connection of amino acids until the last amino acid was connected;

5) 2 g of 20% piperidine as a deprotecting agent was used to remove the protecting group on the last amino acid, and then washing was carried out; and 6) after completion of the reaction, a polypeptide product was washed and shrunk with 5 g of DCM and 5 g of a MeOH solution respectively, the polypeptide product was digested by a lysis buffer (trifluoroacetic acid:1,2-ethanedithiol:water=4:1:1) to obtain a polypeptide, the lysis buffer was separated out by ether, and finally, MS and HLPC analysis was carried out, and the obtained product was sent to purification, where the amino acid sequence of the resulting polypeptide is shown in SEQ ID NO: 1 in sequence listing.

Figure 1:
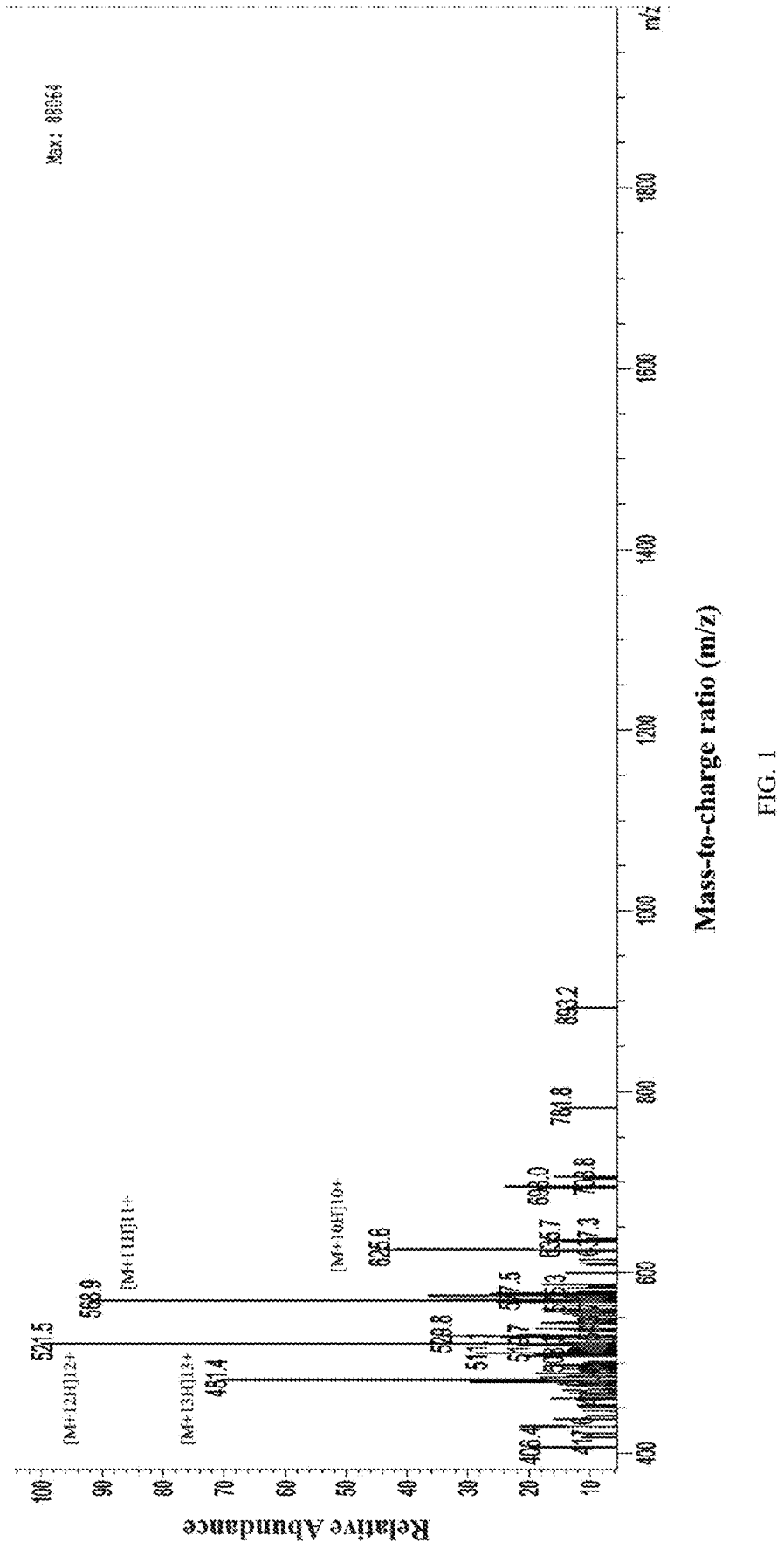
FIG. 1 is an MS test analysis diagram of a reaction product in Example 1.
Figure 2:
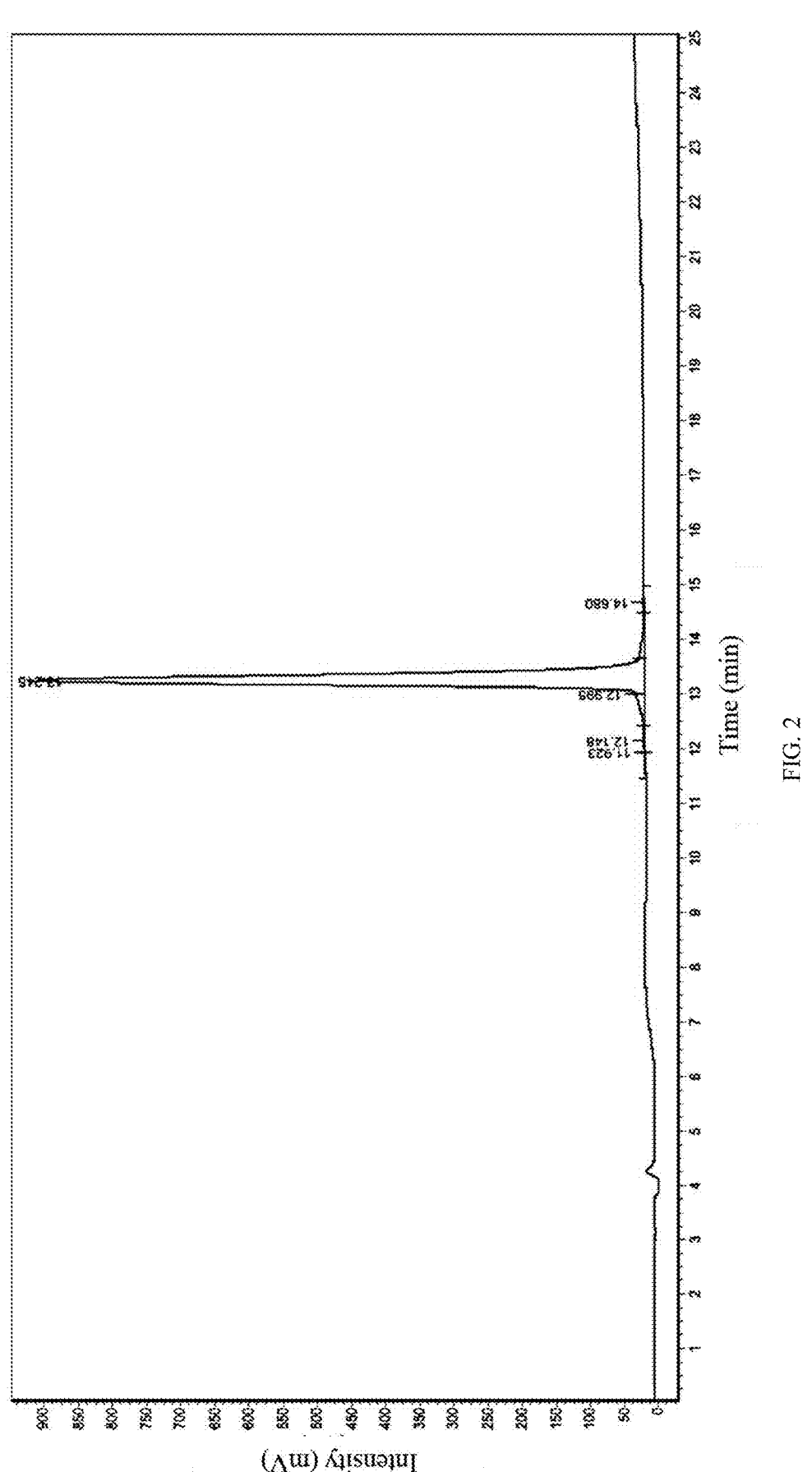
FIG. 2 is an HLPC test analysis diagram of the reaction product in Example 1.

A MS analysis result is shown in FIG. 1, which shows that the molecular weight of the polypeptide is 6244.97;

A HLPC analysis result is shown in FIG. 2, which shows that the purity of the polypeptide is about 95.46%.

Figure 3A:
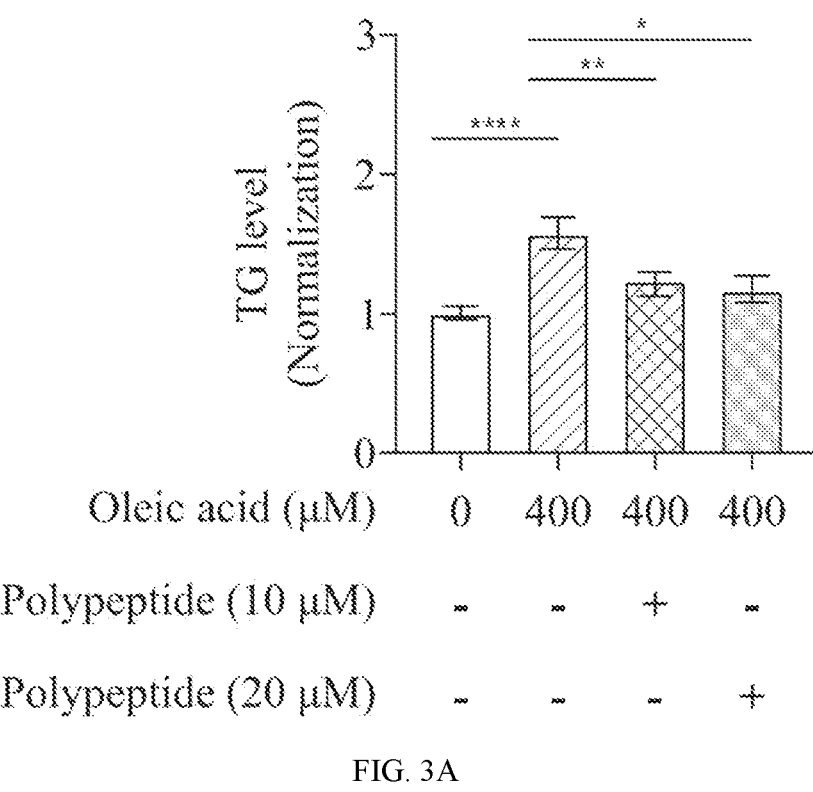
FIGS. 3A-3B are diagrams showing results of quantitative determination of hepatocyte lipids with the polypeptide in Example 1.
Figure 3B:
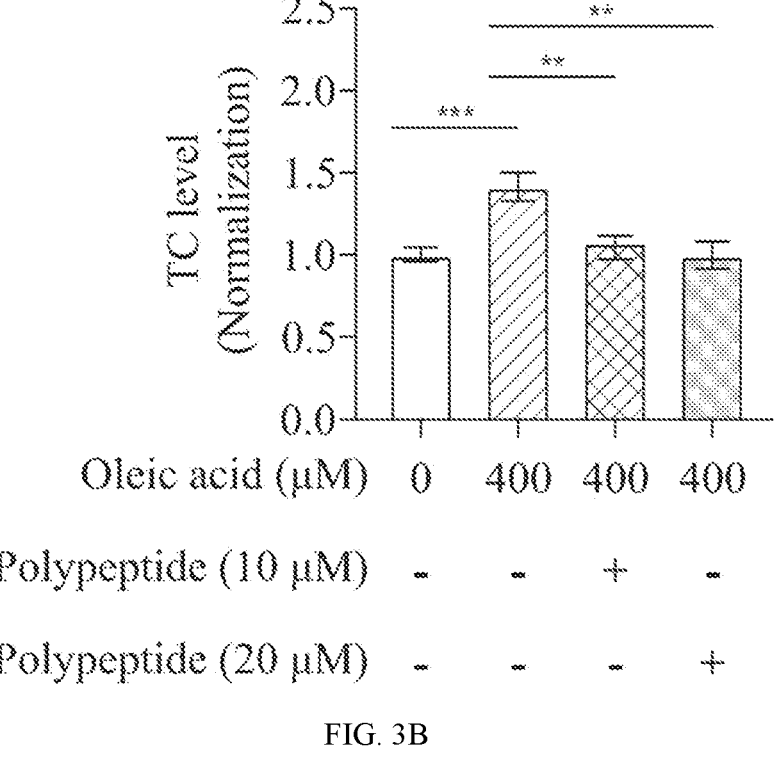
Figure 4:
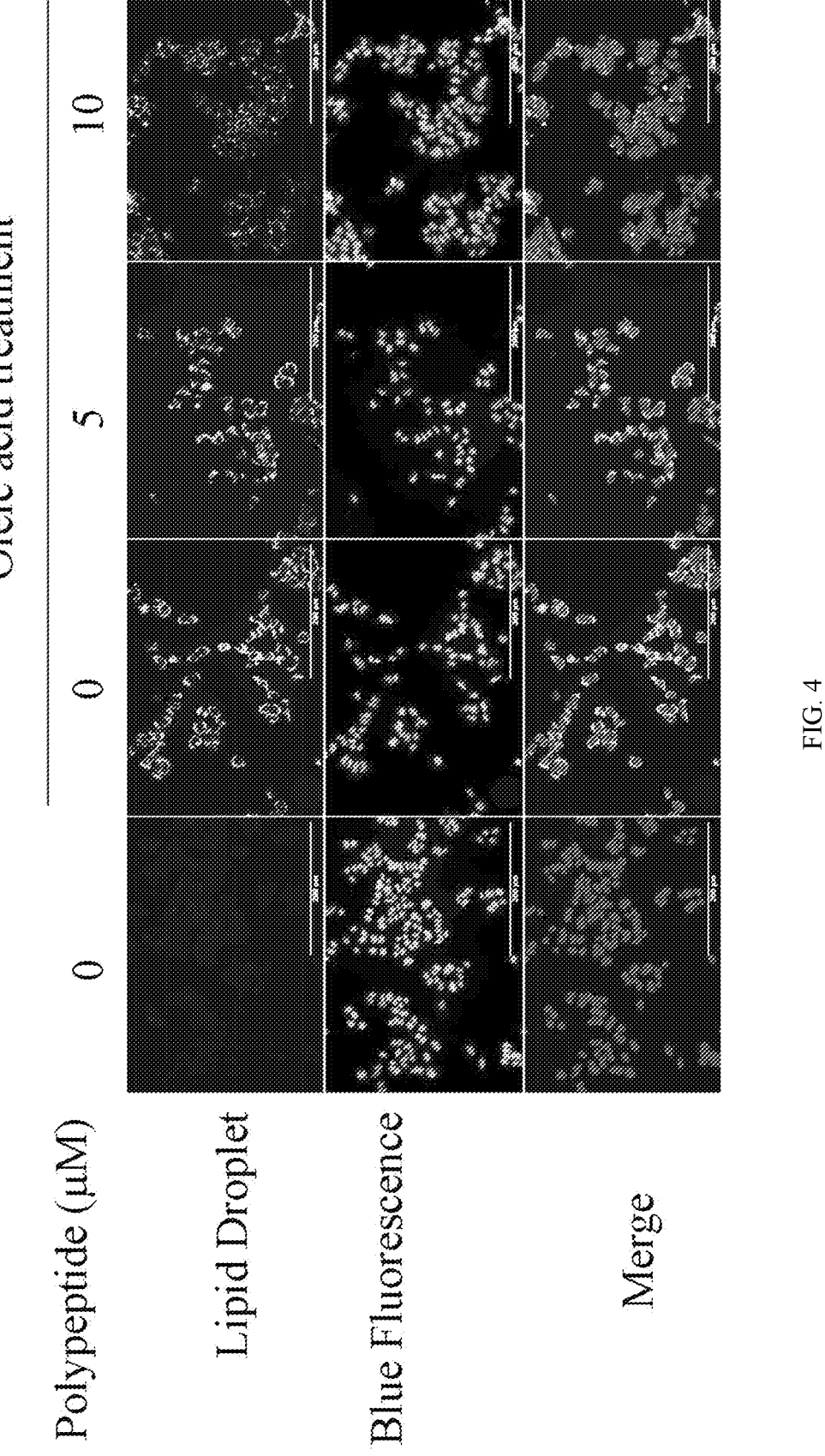
FIG. 4 is a diagram showing fluorescence staining experiments of hepatocytes with the polypeptide in Example 1.

The polypeptide was used to treat hepatocytes for quantification and fluorescence staining experiments on hepatocyte lipids:

400 µM oleic acid (OA) was added into human hepatocarcinoma cells (Huh7) to induce cell fat accumulation, and peptides at different concentrations (10 µM, 20 µM) were added for treatment;

from the quantitative determination of hepatocyte lipids, as shown in FIGS. 3A-3B, it was indicated that the polypeptide can reduce the levels of triglyceride (TG) and total cholesterol (TC) in hepatocytes; and from the fluorescence staining experiments, as shown in FIG. 4, it was indicated that the polypeptide can inhibit the generation of intracellular lipid droplets (LD).

Example 2

A polypeptide applied to inhibition of intracellular lipid accumulation and synthesis thereof:

1) 2 g of Fmoc-lys (boc) Wang resin was put into a reaction column, 3 g of DCM was added to soak the resin for 5 min, 4 g of DMF was used to wash off the DCM, 4 g of dioxane/4M NaOH as a deprotecting agent was used to remove the Fmoc protecting group on the resin where the uncapping time was 20 min, then the resin was washed with the DMF for 6 times, and was subjected to color testing, where a blue color result indicated that the Fmoc was successfully removed, and a colorless result indicated that no reaction occurred and additional uncapping was needed;

2) a second amino acid at free carboxyl terminal was taken, 3 g of a condensing agent DIC and 3 g of DMF were added into the resin reaction column for reaction (gas bubbling), and then the resin was taken for a ninhydrin color testing reaction, where a color result was that the solution was bright yellow, the resin was transparent, and there was no mixed color;

3) 4 g of dioxane/4M NaOH as a deprotecting agent was used to remove the Fmoc protecting group on the second amino acid, and the resin was washed with the DMF for 6 times, and was subjected to color testing, where a blue color result indicated that the Fmoc was successfully removed, and a colorless result indicated that no reaction occurred and additional uncapping was needed;

4) step 2) and step 3) were repeated for connection of amino acids until the last amino acid was connected;

5) 4 g of dioxane/4M NaOH as a deprotecting agent was used to remove the protecting group on the last amino acid, and then washing was carried out; and 6) after completion of the reaction, a polypeptide product was washed and shrunk with 6 g of DCM and 6 g of a MeOH solution respectively, the polypeptide product was digested by a lysis buffer (trifluoroacetic acid:1,2-ethanedithiol:water=5:2:1) to obtain a polypeptide, the lysis buffer was separated out by ether, and finally, the obtained product was sent to purification to obtain the polypeptide of the present disclosure.

Example 3

A polypeptide applied to inhibition of intracellular lipid accumulation and synthesis thereof:

1) 1.5 g of Fmoc-lys (boc) Wang resin was put into a reaction column, 2.5 g of DCM was added to soak the resin for 5 min, 4 g of DMF was used to wash off the DCM, 4 g of pyrrolidone as a deprotecting agent was used to remove the Fmoc protecting group on the resin where the uncapping time was 20 min, then the resin was washed with the DMF for 6 times, and was subjected to color testing, where a blue color result indicated that the Fmoc was successfully removed, and a colorless result indicated that no reaction occurred and additional uncapping was needed;

2) a second amino acid at free carboxyl terminal was taken, 5 g of a condensing agent DIC and 5 g of DMF were added into the resin reaction column for reaction (gas bubbling), and then the resin was taken for a ninhydrin color testing reaction, where a color result was that the solution was bright yellow, the resin was transparent, and there was no mixed color;

3) 4 g of pyrrolidone as a deprotecting agent was used to remove the Fmoc protecting group on the second amino acid, and the resin was washed with the DMF for 6 times, and was subjected to color testing, where a blue color result indicated that the Fmoc was successfully removed, and a colorless result indicated that no reaction occurred and additional uncapping was needed;

4) step 2) and step 3) were repeated for connection of amino acids until the last amino acid was connected;

5) 4 g of pyrrolidone as a deprotecting agent was used to remove the protecting group on the last amino acid, and then washing was carried out; and 6) after completion of the reaction, a polypeptide product was washed and shrunk with 8 g of DCM and 8 g of a MeOH solution respectively, the polypeptide product was digested by a lysis buffer (trifluoroacetic acid:1,2-ethanedithiol:water=6:1:2) to obtain a polypeptide, the lysis buffer was separated out by ether, and finally, the obtained product was sent to purification to obtain the polypeptide of the present disclosure.

Example 4

A polypeptide applied to inhibition of intracellular lipid accumulation and synthesis thereof:

1) 3 g of Fmoc-lys (boc) Wang resin was put into a reaction column, 4 g of DCM was added to soak the resin for 5 min, 5 g of DMF was used to wash off the DCM, 6 g of concentrated ammonia as a deprotecting agent was used to remove the Fmoc protecting group on the resin where the uncapping time was 20 min, then the resin was washed with the DMF for 6 times, and was subjected to color testing, where a blue color result indicated that the Fmoc was successfully removed, and a colorless result indicated that no reaction occurred and additional uncapping was needed;

2) a second amino acid at free carboxyl terminal was taken, 5 g of a condensing agent DIC and 5 g of DMF were added into the resin reaction column for reaction (gas bubbling), and then the resin was taken for a ninhydrin color testing reaction, where a color result was that the solution was bright yellow, the resin was transparent, and there was no mixed color;

3) 6 g of concentrated ammonia as a deprotecting agent was used to remove the Fmoc protecting group on the second amino acid, then the resin was washed with the DMF for 6 times, and was subjected to color testing, where a blue color result indicated that the Fmoc was successfully removed, and a colorless result indicated that no reaction occurred and additional uncapping was needed;

4) step 2) and step 3) were repeated for connection of amino acids until the last amino acid was connected;

5) 6 g of concentrated ammonia as a deprotecting agent was used to remove the protecting group on the last amino acid, and then washing was carried out; and enous polypeptides can inhibit the generation of intracellular lipid droplets (LD).

The exclusion of interference of Mito-DsRed with the experimental results as above has proved that the polypeptide-DsRed, rather than its carrier Mito-DsRed, is responsible for the experimental results.

SEQUENCE LISTING

```
<160> NUMBER OF SEQ ID NOS: 1

<210> SEQ ID NO 1
<211> LENGTH: 53
<212> TYPE: PRT
<213> ORGANISM: Artificial Sequence
<220> FEATURE:
<223> OTHER INFORMATION: The sequence is synthesized.

<400> SEQUENCE: 1

Met Glu Pro Gly Gly Ala Arg Leu Arg Leu Gln Arg Thr Glu Gly Leu
1               5                   10                  15

Gly Gly Glu Arg Glu Arg Gln Pro Cys Gly Asp Gly Asn Thr Glu Thr
            20                  25                  30

His Arg Ala Pro Asp Leu Val Gln Trp Tyr Gly Arg Lys Lys Arg Arg
        35                  40                  45

Gln Arg Arg Arg Lys
    50
```

6) after completion of the reaction, a polypeptide product was washed and shrunk with 10 g of DCM and 10 g of a MeOH solution respectively, the polypeptide product was digested by a lysis buffer (trifluoroacetic acid: 1,2-ethanedithiol:water=7:2:2) to obtain a polypeptide, the lysis buffer was separated out by ether, and finally, the obtained product was sent to purification to obtain the polypeptide of the present disclosure.

Figure 5:
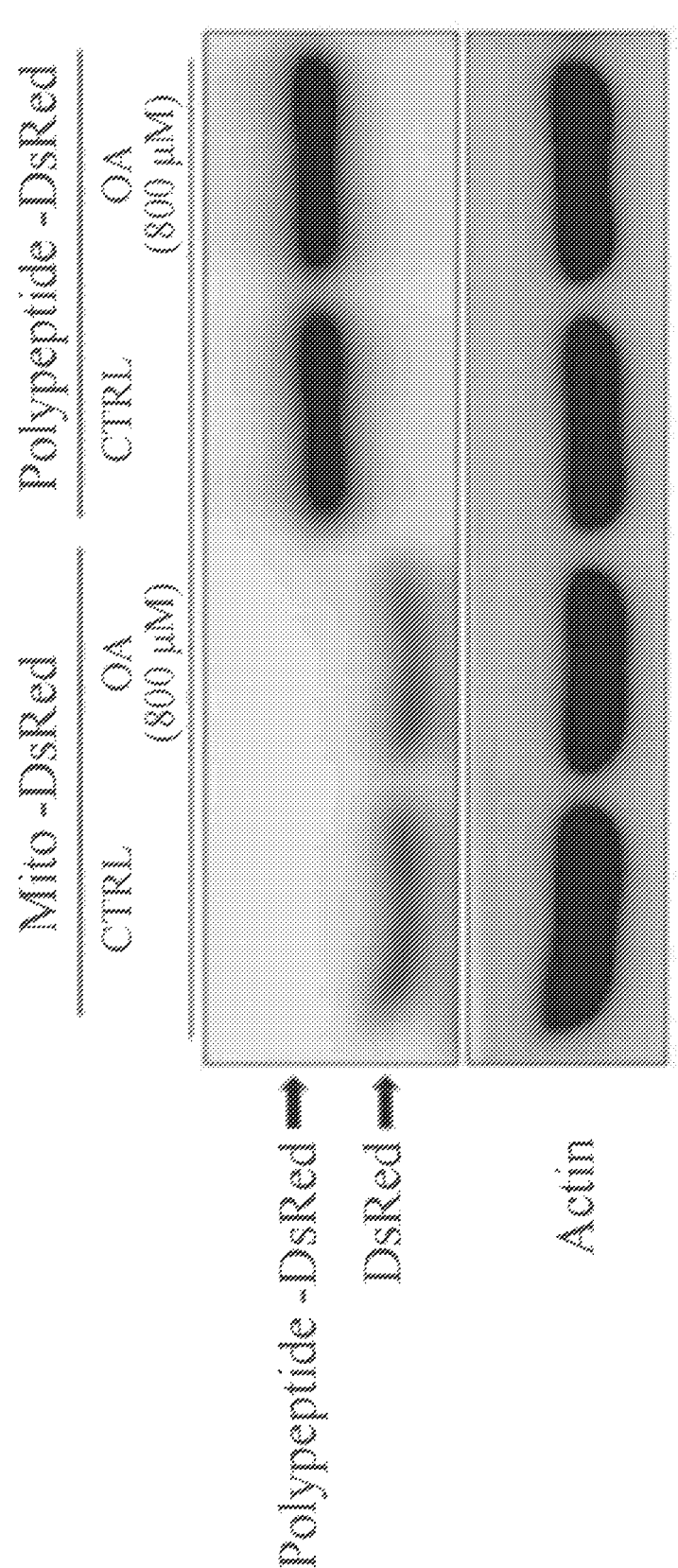
FIG. 5 is a diagram showing western blot results after polypeptide-DsRed and Mito-DsRed plasmids are transfected into hepatocytes.
Figure 6:
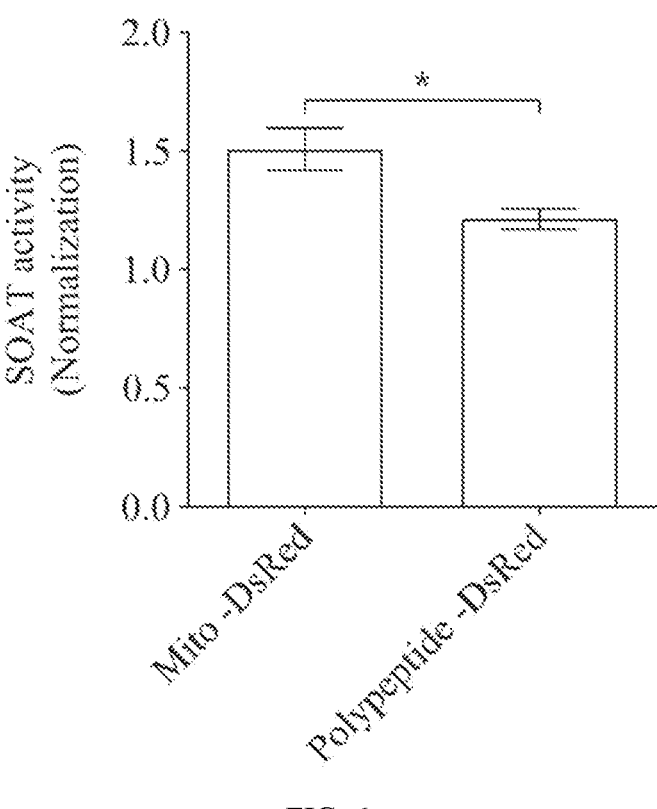
FIG. 6 is a diagram showing SOAT (sterol o-acyltransferase) activity assay results after polypeptide-DsRed and Mito-DsRed plasmids are transfected into hepatocytes.
Figure 7A:
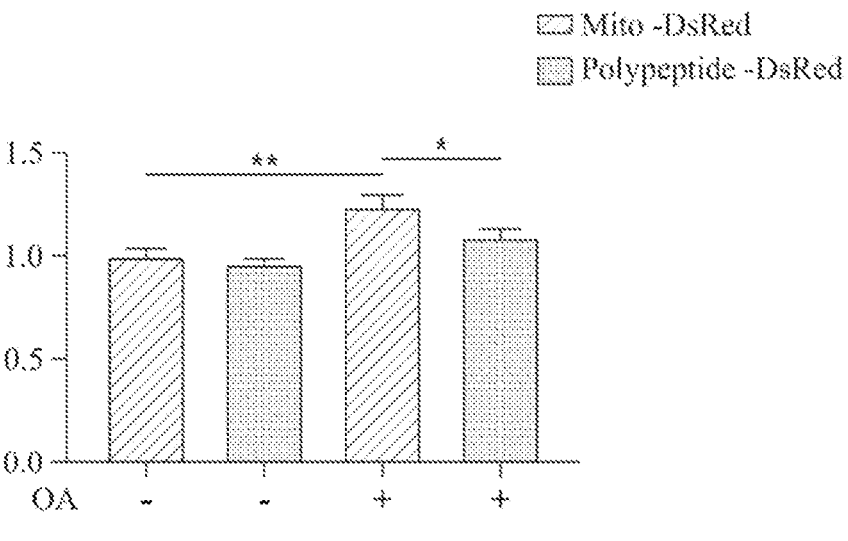
FIGS. 7A-7B are diagrams showing lipid determination results after polypeptide-DsRed and Mito-DsRed plasmids are transfected into hepatocytes.
Figure 7B:
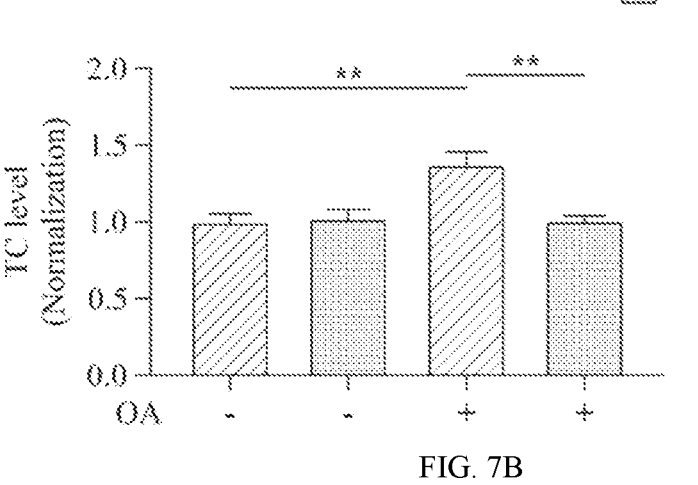
Figure 8:
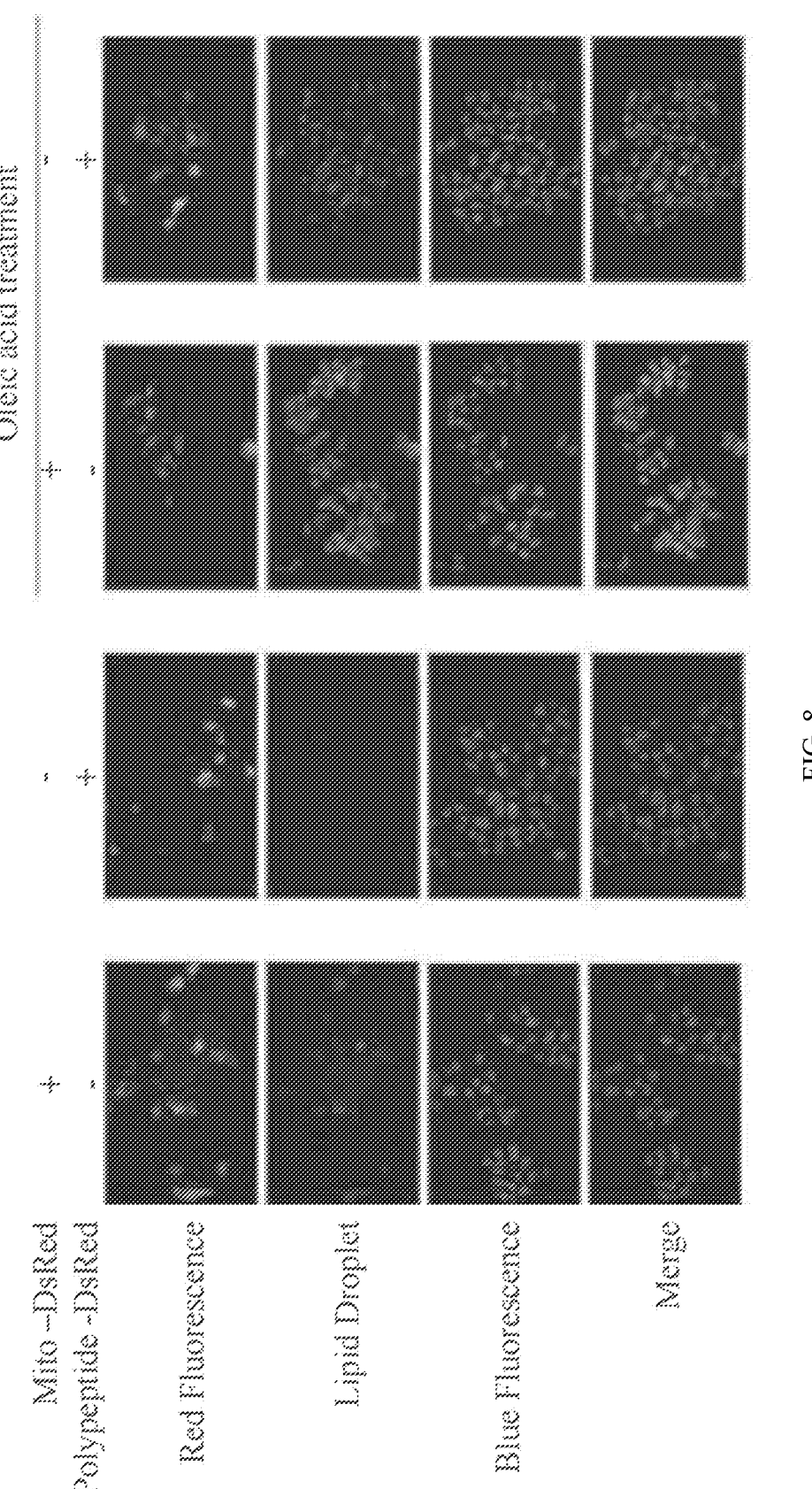
FIG. 8 is a diagram showing experimental results of fluorescence staining of Lipid Droplets (LDs) after polypeptide-DsRed and Mito-DsRed plasmids are transfected into hepatocytes.

An experimental test will be carried out below from polypeptide-DsRed and Mito-DsRed plasmids (which are cloning vector plasmids of the polypeptide of the present disclosure, and are used as a reference to exclude empty plasmids) by combining the polypeptide with a red fluorescence protein:

1) the polypeptide-DsRed and Mito-DsRed plasmids were transfected into hepatocytes, and 800 μM oleic acid (OA) was added to induce cellular fat accumulation; and as shown in FIG. 5, by western blot, it was confirmed that the polypeptide-DsRed plasmids were successfully expressed in the hepatocytes;

2) the polypeptide-DsRed and Mito-DsRed plasmids were transfected into hepatocytes, and 800 μM oleic acid (OA) was added to induce cellular fat accumulation; and as shown in FIG. 6, by SOAT (sterol o-acyltransferase) activity assay, it was found that the endogenous polypeptides can reduce the SOAT activity;

3) the polypeptide-DsRed and Mito-DsRed plasmids were transfected into hepatocytes, and 400 μM oleic acid (OA) was added to induce cellular fat accumulation; as shown in FIGS. 7A-7B, by determination of lipids, it was found that the endogenous polypeptides can reduce the levels of triglyceride (TG) and total cholesterol (TC) in hepatocytes; and as shown in FIG. 8, by a Lipid Droplet (LD) fluorescent staining experiment, it was confirmed that the endog-

What is claimed is:

1. A polypeptide which inhibits intracellular lipid accumulation, comprising the amino acid sequence of SEQ ID NO: 1.

2. A polypeptide drug which inhibits intracellular lipid accumulation, comprising the amino acid sequence of SEQ ID NO: 1.

3. A synthesis method of a polypeptide comprising SEQ ID NO: 1 applied to an inhibition of an intracellular lipid accumulation, comprising the following steps:

1) Soaking a resin in an organic solution, washing off the organic solution from the resin, removing a protecting group on the resin with a deprotecting agent to obtain a first resulting resin, and washing the first resulting resin;

2) Taking a second amino acid at a free carboxyl terminal and adding a condensing agent and N,N-dimethylformamide (DMF) into the first resulting resin for a reaction to obtain a second resulting resin, and then taking the second resulting resin for a first color testing;

3) Removing a protecting group on the second amino acid with the deprotecting agent to obtain a resulting product, and washing the resulting product;

4) Repeating step 2) and step 3) for a connection of amino acids until a last amino acid is connected;

5) Removing a protecting group on the last amino acid with the deprotecting agent to obtain a third resulting resin, washing the third resulting resin and then subjecting the third resulting resin to a second color testing; and 6) After a completion of the reaction, washing and shrinking a polypeptide product with a solution, digesting the polypeptide product by a lysis buffer to obtain a digested polypeptide of SEQ ID NO: 1, and finally, analyzing and purifying the digested polypeptide.

4. The synthesis method of the polypeptide according to claim 3, wherein the resin in step 1) comprises Fmoc-lys (boc) Wang resin.

5. The synthesis method of the polypeptide according to claim 3, wherein the deprotecting agent in step 1), step 3) and step 5) comprises amine-base solvents.

6. The synthesis method of the polypeptide according to claim 5, wherein the deprotecting agent comprises 20% piperidine.

7. The synthesis method of the polypeptide according to claim 3, wherein the first color testing in step 2) is a ninhydrin color testing reaction, and a color result is that a resulting color testing reaction solution is bright yellow, the second resulting resin is transparent, and there is no mixed color.

8. The synthesis method of the polypeptide according to claim 3, wherein the second color testing in step 5) is a ninhydrin color testing reaction, a blue color result of the second color testing indicates that the protecting group on the last amino acid is successfully removed, and a colorless result indicates that no reaction occurs and an additional uncapping operation is needed.

9. The synthesis method of the polypeptide according to claim 3, wherein the solution in step 6) comprises dichloromethane (DCM) and MeOH.

10. The synthesis method of the polypeptide according to claim 3, wherein the lysis buffer in step 6) is a mixed solution of trifluoroacetic acid, 1,2-ethanedithiol, and water.

11. The synthesis method of the polypeptide according to claim 5, wherein the amine-base solvents comprise one of piperidine, concentrated ammonia, dioxane/4M NaOH, ethanolamine, cyclohexylamine, morpholine, pyrrolidone, and 1,8-Diazabicyclo[5,4,0]undec-7-ene (DBU).

\* \* \* \* \*